United States Patent
Yundt-Pacheco

(10) Patent No.: US 7,010,448 B1
(45) Date of Patent: *Mar. 7, 2006

(54) METHOD AND STRUCTURE FOR MITIGATING INSTRUMENTATION DIFFERENCES

(75) Inventor: John C. Yundt-Pacheco, Fairview, TX (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/519,224

(22) Filed: Mar. 6, 2000

(51) Int. Cl.
*G01D 18/00* (2006.01)
(52) U.S. Cl. .......................... 702/85; 436/49
(58) Field of Classification Search ................ 436/49; 600/300, 555; 702/85, 179, 84, 194, 77; 101/426; 356/327, 319; 700/73, 95; 375/224; 382/145; 73/583; 236/47; 324/76.11
See application file for complete search history.

(56) References Cited

U.S. PATENT DOCUMENTS

| | | | | |
|---|---|---|---|---|
| 3,958,509 A | * | 5/1976 | Murray et al. | 101/350.1 |
| 5,532,941 A | * | 7/1996 | Lin | 702/84 |
| 5,646,046 A | * | 7/1997 | Fischer et al. | 436/49 |
| 6,334,099 B1 | * | 12/2001 | Grace et al. | 702/194 |
| 6,507,765 B1 | * | 1/2003 | Hopkins et al. | 700/95 |

* cited by examiner

*Primary Examiner*—Michael Nghiem
*Assistant Examiner*—Xiuqin Sun
(74) *Attorney, Agent, or Firm*—J. David Wharton; Stinson Morrison Hecker LLP

(57) ABSTRACT

A system for mitigating instrumentation differences in laboratory instruments includes one or more groups of laboratory instruments in communication with a normalization server over a network. Each group of instruments communicates output data to the normalization server which then presents normalized data to the groups of laboratory instruments. Various exemplary embodiments of the system and associated methods are provided.

1 Claim, 4 Drawing Sheets

| SPECIMEN | LAB | CONTROL | |
|----------|-----|---------|----|
| 1 | 98 | 254 | ← 34 |
| 2 | 59 | 162 | ← 36 |
| 3 | 144 | 388 | ← 38 |
| 4 | 129 | 362 | ← 40 |
| 5 | 34 | 107 | ← 42 |

| SPECIMEN | LAB | CONTROL | LAB NORMALIZED |
|---|---|---|---|
| 1 | 98 | 254 | 268 |
| 2 | 59 | 162 | 166 |
| 3 | 144 | 388 | 389 |
| 4 | 129 | 362 | 350 |
| 5 | 34 | 107 | 100 |

FIG. 6.

METHOD AND STRUCTURE FOR MITIGATING INSTRUMENTATION DIFFERENCES

TECHNICAL FIELD

In general, the present invention relates to instrumentation data analysis, and in particularly, to a method and device for mitigating instrumentation differences in laboratory equipment.

BACKGROUND OF THE INVENTION

Generally, data outputs from a laboratory instrument testing of a subject sample may be utilized to monitor the performance of the instrument or to provide a comparison set of results for the subject being tested. Specifically, the subject sample being tested can include a standardized external quality control sample distributed by a testing organization or an individual patient sample to be tested and analyzed. For example, if the subject sample is a standardized external quality control sample, the test results from the instrument allow the laboratory to ensure that the instrument is properly functioning by comparing the instrument data with peer group results of the same sample. Similarly, if the subject sample is from an individual patient, one or more tests provide a comparison set of data to measure the progress of the patient. With either type of subject sample, the results from the test are critical to the operation of the testing laboratory. Moreover, the subject testing can be conducted by one or more instruments to form a laboratory testing group.

With regard to the testing of a external quality control sample, a conventional method of control group testing entails testing and directly comparing the results to a peer group becomes deficient if the peer group is too small. For example, if a group of laboratory instruments testing a proficiency sample includes data from only eight instruments, the relatively small number of instrument results do not provide an adequate peer group to construct a proper range of expected results. Accordingly, in such a scenario, it would be advantageous to utilize a larger peer group, such as 400 or 500 instruments from a plurality of laboratories, to develop a proper range of results. However, under the conventional method, differences between the instruments, in the form of calibration differences, statistical behavior differences and/or test method differences, can yield differences between the laboratory group results and the peer group results. Thus, the conventional method of a direct comparison between the results of the two groups could be either impossible or erroneous.

With regard to the testing of a patient subject sample, the conventional method of testing and directly comparing the data results between a first and second sample can become deficient if the patient group is mobile and there are differences between the laboratory instruments. Specifically, a patient sample may be tested by a first group of laboratory instruments yielding a first set of results. If a second test is conducted by a second group of laboratory instruments, differences between the instruments of the two groups may cause a reviewer to believe there is a larger discrepancy between the results then there actually is.

For example, a first test of a patient sample indicates that the amount of a substance in the patient test sample was 100. If the second test conducted by another laboratory group indicates that the amount of the substance in the patient sample is 384, a direct comparison of the two results would indicate that the patient sample had a substantial increase in the amount of the substance present. However, it could be possible that the actual difference in the amount of the substance in the sample is minimal and that large difference is due primarily to the differences (e.g. calibration differences) between the two laboratory instrument groups. Accordingly, the conventional method of a direct comparison would cause an improper analysis.

Thus, there is a need for a method and device for facilitating the comparison of laboratory group results with peer group quality control results by mitigating differences in the instruments. Additionally, there is a need for a method and device allowing patient sample results to be normalized for comparison by reducing differences between the groups.

SUMMARY OF THE INVENTION

The present invention satisfies the above-described need by providing a method and system for mitigating differences in laboratory instrument outputs by the normalization of the laboratory instrument output data in accordance with a control group.

Generally described, the present invention provides a method for normalizing a group of laboratory instruments. In accordance with the method, data indicative of control specimen outputs is obtained for the group of laboratory instruments, and the data is normalized according to a control group.

In another aspect of the present invention, a method for normalizing two or more groups of laboratory instruments is provided. In accordance with the method, a first of the two or more groups of laboratory instruments control specimen outputs is obtained, a second of the two or more groups of laboratory instruments control specimen outputs is obtained, and the control specimen outputs from the first and second groups of laboratory instruments are normalized.

In a further aspect of the present invention, a system for normalizing groups of laboratory instruments is provided. The system includes one or more groups of laboratory instruments and a normalization server in communication with the groups of laboratory instruments. Additionally, the groups of laboratory instruments send data indicative of outputs to the normalization system and the normalization system outputs normalized outputs to the groups of laboratory instruments.

In yet another aspect of the present invention, a method for standardizing instrument results from a plurality laboratory instruments is provided. In accordance with the method, testing specimen data is obtained from a first of a group of laboratory instruments, the first laboratory instrument testing specimen data is normalized according to a first normalization curve, and the first laboratory instrument data is adjusted according to the first normalization curve.

By normalizing the output from a laboratory group, the present invention reduces the statistical differences between two or more laboratory group results and allows meaningful data analysis.

BRIEF DESCRIPTION OF THE DRAWING

The present invention is described in detail below with reference to the attached drawing figures, wherein:

FIG. 6 is a chart illustrating a comparison of the output results from a laboratory group test and output value from a control group of FIG. 3 and the normalized laboratory group outputs in accordance with the present invention.

DETAILED DESCRIPTION OF THE INVENTION

The present invention provides a method and device for mitigating instrumentation differences in laboratory equipment outputs by normalizing the output from the group of laboratory instruments to a control group. Preferably, the present invention is implemented in a computing environment commensurate with the number of laboratory instruments in the system and the quantity of data being normalized. The invention is operable with numerous general purpose or special purpose computing system environments. Examples of well known computing systems that may be suitable for use with the invention include personal computers, server computers, hand-held or lap top devices, multiprocessor systems, network personal computers, minicomputers, and mainframe computers. As would be readily understood by someone skilled in the art, additional computing environments are within the scope of the present invention.

Figure 1:
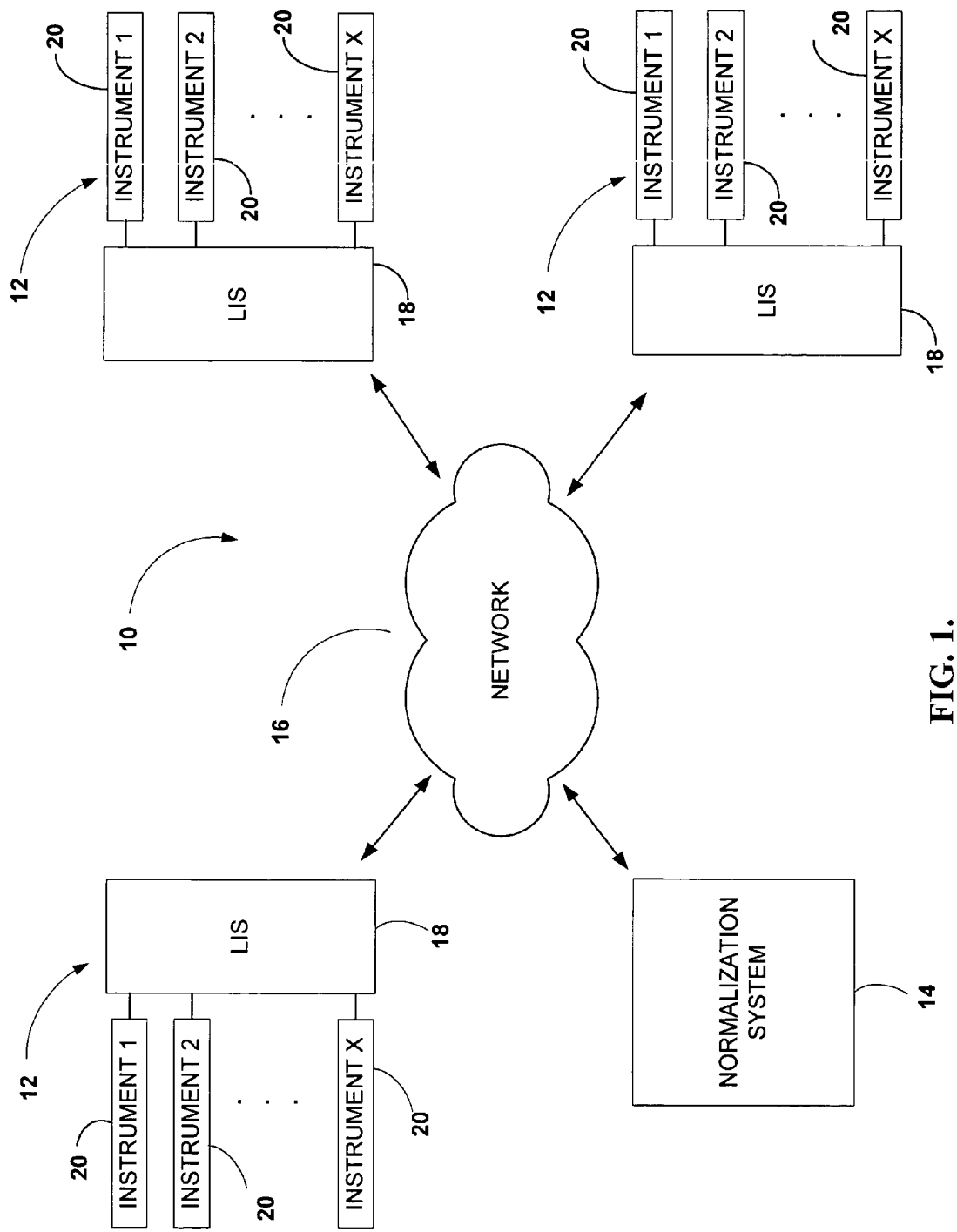
FIG. 1 is a block diagram illustrating the interaction between one or more groups of laboratory instruments and a normalization server in accordance with the teachings of the present invention.

FIG. 1 is a block diagram illustrative of the normalization system of the present invention, designated generally by the reference number 10. The normalization system 10 includes one or more laboratory instrument groups 12 in communication with a normalization server 14 via a communications network 16.

Preferably, each laboratory instrument group 12 includes a laboratory information system (LIS) 18, which is direct communication with one or more laboratory instruments 20. As would be readily understood, the laboratory instrument groups 12 may be remote from each other and from the normalization server 14. Additionally, the laboratory instruments 20 connected to the LIS 18 may also be remote from each other and from the LIS 18. Moreover, the laboratory instruments 20 may include identical instruments from the same manufacturer, different instruments from the same manufacturer, or instruments from a variety of manufacturers. Preferably, the normalization server includes one or more computing devices to carry out the functions of the normalization server in accordance with the present invention.

Preferably, the network 16 includes an Internet-based network, with the normalization server 14 linked to the groups of laboratory instruments via a web site interface. As would be understood, the network can include any variety and/or combination of Local Area Networks (LAN) or Wide Area Networks (WAN) to facilitate communication between the laboratory groups and the normalization server. Additionally, the network 16 may include a dedicated communications link, such as dial-up telephone modem connection, between the groups of laboratory instruments 12 and the normalization server 14.

Figure 2:
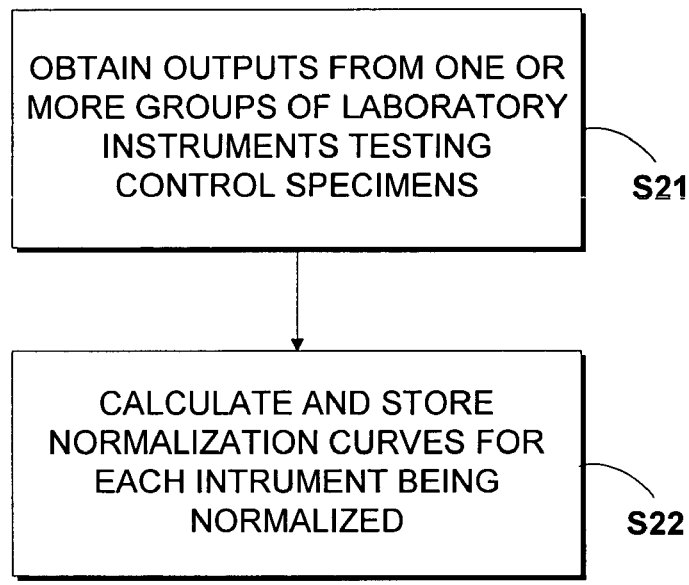
FIG. 2 is a flow diagram of a preferred normalization setup method implemented by a normalization server in accordance with the present invention.
Figure 3:
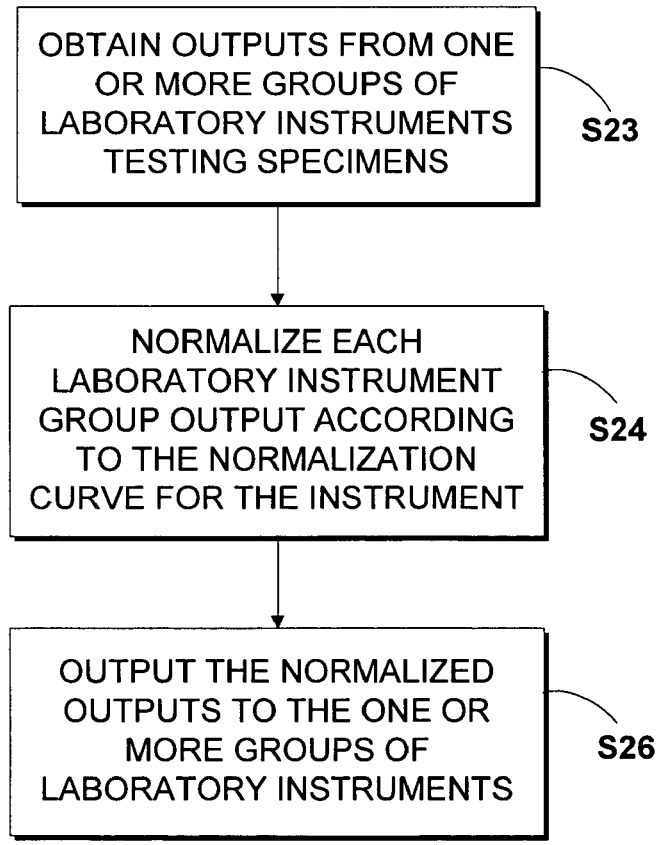
FIG. 3 is a flow diagram of a preferred normalization usage method implemented by a normalization server in accordance with the present invention.

FIGS. 2 and 3 are flow diagrams of a preferred normalization method implemented by the normalization server in accordance with the present invention. The present invention utilizes this procedure to establish normalization curves for known ranges of results and utilize thes curves for future external quality control testing and patient sample testing. Preferably, the normalization method is characterized into a normalization setup portion (FIG. 2) and a normalization usage portion (FIG. 3). The normalization setup portion preferably entails the normalization server receiving test control specimens outputs from one or more groups of laboratory instruments and generating a normalization curve for each instrument. Accordingly, the normalization usage portion entails the normalization server receiving test data (either external quality control data or patient sample data) and normalizing the data according to the individual normalization curve for the testing instrument.

FIG. 2 is a flow diagram of a preferred normalization setup method in accordance with the present invention. As a general rule, laboratory instrument groups must constantly test and analyze test control specimens from external quality control organization. At S21, the normalization server obtains outputs from one or more groups of laboratory instruments testing control specimens. Preferably, the normalization server can receive the laboratory instrument outputs in a variety of manners. In a first embodiment, the normalization server includes an Internet-based web site which receives data from each group of laboratory instruments. In such an embodiment, the LIS (FIG. 1) from each group communicates with the normalization server and sends the output data from each laboratory instrument in a manner which is formatted to facilitate normalization. Alternatively, the web site may include a manual input screen that allows the data to be manually entered via the web site.

In a second embodiment, a direct communications link, such as a telephone modem connection, is established by the LIS or the normalization server for the purpose of transferring the output data. Additionally, prior to sending the laboratory instrument output data to the normalization server, the LIS may format the data in a manner to facilitate its processing alternatively, a graphical interface may be established between the LIS and the normalization server, such as an input screen, to allow the manual entry of the output data over the communications link to the normalization server. In a third embodiment, the output from the laboratory instrument group may be physically sent to the normalization server provider and entered manually via a plurality of data input methods. As would be understood, alternative data transfer embodiments or a combination of the above mentioned embodiments are within the scope of the present invention.

Once the test specimen output data has been obtained by the normalization server at S21, the normalization server calculates and stores normalization curves for each laboratory instrument being normalized at S22. Preferably, the normalization server utilizes a variety of normalization methods dependant on the output data and the type of normalization desired to construct the normalization curve. For example, in a first embodiment the normalization server utilizes a liner regression method to normalize the data. In a second embodiment, the normalization server utilizes a nonlinear regression method. In a third embodiment, the normalization server applies a spline to normalize the data.

Preferably, the normalization server receives the group instrument control specimen data and the control group data for the same control specimen and applies the variety of normalization methods to construct numerous normalization curves. Then, the normalization server measures the relative error between the actual data points and the normalized curve. For example, assume data from a group of laboratory instruments follows a generally non-linear trend. As the data is received, the normalization server would utilize a linear regression, a non-linear regression, a spline and any other normalization method to map the data points as a curve. Because the data is generally non-linear, however, it is likely that the linear regression would have a greater curve error than the non-linear regression curve. Generally, curve error can be defined as the difference in values from an actual data point and the calculated data point of the curve.

Accordingly, the normalization server would measure the curve error for each of the generated curves and select the curve with the least average curve error per data point. Alternatively, the normalization server may select the curve with the least cumulative curve error for all the data points. Moreover, the group of laboratory instruments may also designate a default type of normalization method irrespective of the curve error analysis. Once a preferred normalization curve is constructed, the normalization saves the curve for future use. As would be readily understood, the determination by the normalization server of a best fitting curve may utilize additional normalization methods and may utilize additional statistical calculations (e.g. eliminating extreme data points). All are within the scope of the present invention.

FIG. 3 is a flow diagram of a preferred normalization usage method in accordance with the present invention. Once the normalization setup method has been executed (FIG. 2), the normalization server utilizes the individual curve for each instrument to normalize output data. At S23, the normalization server obtains outputs from one or more groups of laboratory instruments testing specimens which can be external quality control specimens or patient testing samples. Similar to the obtaining step illustrated at S21, the normalization server can obtain the testing specimen data from the laboratory instruments or LIS in a variety of manners.

Once the testing data has been obtained at S23, the data is normalized according to the previously stored normalization curve for each instrument at S24. Preferably, the normalization server recalls the calculated normalization curve and maps the inputted data according to the preferred curve. Alternatively, the normalization server may recall all the calculated normalization curves, and maps the data into all the curves. Accordingly, a determination of the best curve for the specific data points may be selected according to curve error or user choice at that point. All are considered within the scope of the present invention.

Once the output data has been normalized according to the normalization curves at S24, the normalization server outputs the normalized data to one or more groups of laboratory instruments at S26. Dependant on the needs of each group of laboratory instruments, the outputting step can encompass one or more methods. In a first embodiment, the normalization server displays the normalized output by group of laboratory instruments on a central network for access by the specific group of laboratory instruments or by the entire network. In a second embodiment, the normalization server outputs the data directly via a network or a direct communication line to the LIS (FIG. 1) of the laboratory instrument group. In a third embodiment, the normalization server outputs the normalized data to a memory for archiving purposes or for later transmittal to the laboratory instrument group. Additionally, the normalization server may utilize any combination of the outputting embodiments to relay the outputted data in more than one manner.

Figures 4, 5:
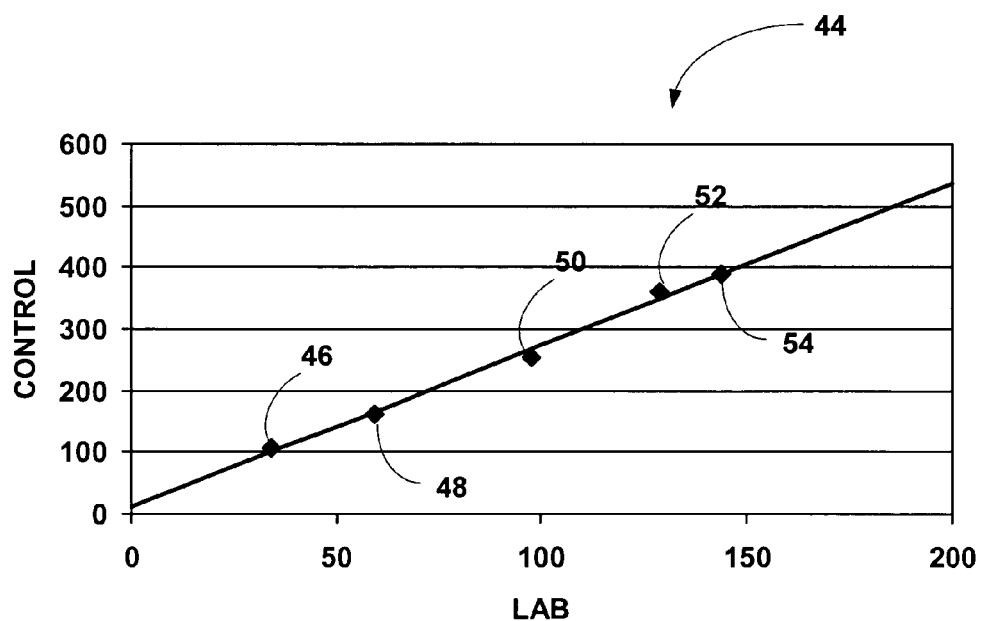
FIG. 4 is a chart illustrating a comparison of output results from a laboratory group tests and output values from a control group.
FIG. 5 is illustrative of a line fit plot applied to the laboratory group test output of FIG. 3.
Figure 6:
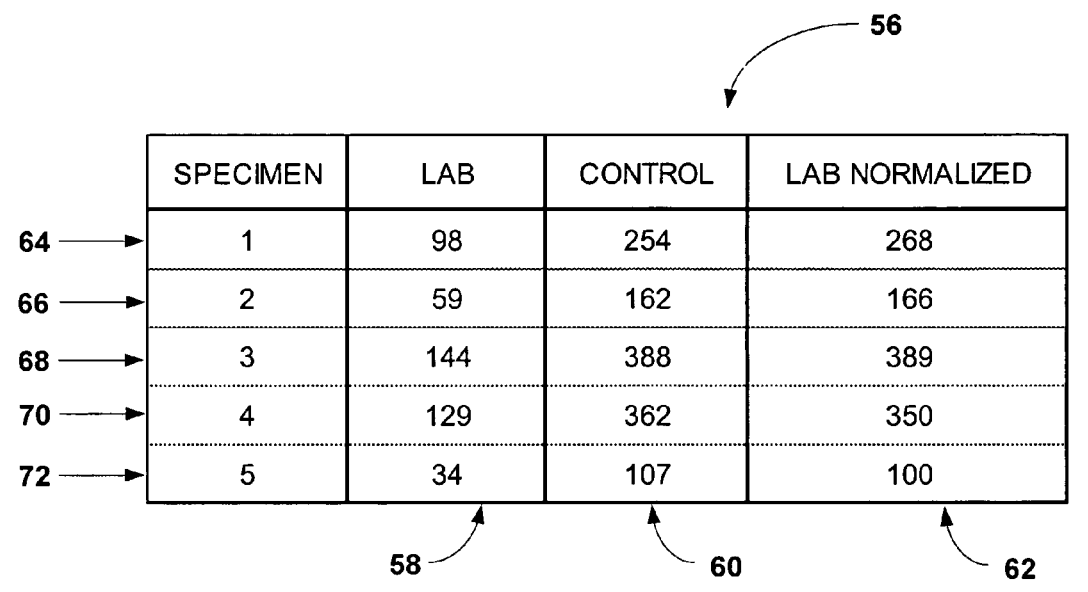

FIGS. 4–6 are charts and graphs illustrating the "mapping" of results from a group of laboratory instruments into a control group of results in accordance with the methods and structures of the present invention. With reference to FIG. 4, chart 28 illustrates outputs for five specimens from a group of laboratory instruments in a second column 30 and outputs for the same specimen from a control group in a third column 32. As can be seen, a direct comparison of the results from the laboratory instrument outputs and the control group outputs yields a big discrepancy in values. For example, the output results for specimen 1 in row 34 indicate that the laboratory group result is "98", while the control group result for the same specimen is "254". Accordingly, the resulting difference between the two groups appears to be 156. Likewise, a comparison of rows 36–42 discloses apparent differences of 103, 244, 233 and 73 respectively. Under a conventional analysis, the results from the group 30 would be considered erroneous or incompatible with the control group 32. However, the present invention allows the lab group results to be rectified by a mapping of the group of laboratory results into the control group results.

FIG. 5 is illustrative of a line fit plot 44 applied to the group of laboratory results (FIG. 4) to map the data into the control group results in accordance with the present invention. Specifically, based on the application of a linear regression method, an equation of $y=2.63x+10.4$ is calculated to be a preferred normalization curve in the normalization setup method (FIG. 2). As illustrated in FIG. 5, the corresponding line 44 generates five data points, 46–54, corresponding to the original laboratory group results. For example, data point 46 corresponds to the fifth specimen result (column 42 of FIG. 4) which is "34" on the x-axis of the line fit plot 44. Additionally, the data point 46 indicates the mapped value corresponding to the control group results is "100", allowing the two groups of results to be better compared.

FIG. 6 is a chart 56 illustrating the original laboratory group instrument outputs in a second column 58, the outputs of a control group in a third column 60, and the normalized outputs of the laboratory instrument outputs in a fourth column 62. As illustrated in rows 64–72, the normalized values of the laboratory instrument outputs 62 are much closer to the control group values 60, allowing a better comparison of the data. For example, the value for specimen 1 in column 64 indicates that the original lab result was "98" while the control group for the specimen was "254". As mapped by the method and structure of the present invention, however, the normalized value is "268", better reflecting the actual differences in testing values between the laboratory group and the control group.

The system and method of the present invention can be implemented in a variety of testing embodiments. In a first embodiment, a group of laboratory instruments run tests on a external quality control specimen which is provided by a testing facility. As would be understood, to provide quality control testing of the particular instruments, the results from the laboratory group are compared to a peer group running tests on specimen samples originating from the same lot. However, statistical differences between the instruments (especially if the groups have instruments made by different manufacturers) may cause the outputs to vary significantly. In a conventional testing system, the results typically cannot be compared and consequently, the laboratory instrument groups cannot utilize the larger common peer group. In contrast, however, the present invention generates normalization curves allowing the laboratory instrument group results to be normalized with the control group output by utilizing normalization curves calculated from previous external quality control test specimen data. This method allows a laboratory instrument group facilitator to compare its output data to a larger peer group because differences between groups can be mitigated. Moreover, the mapping of the laboratory output allows the laboratory instrument group to add their data to the peer group as well.

In an alternative embodiment, the method and device of the present invention may also be utilized to provide direct comparison of lab results from two or more laboratory instrument groups. For example, a laboratory patient may have a series of tests conducted at a first laboratory group and the same series of tests conducted at a second laboratory group. If the laboratory testing groups have statistical differences in their outputs, the conventional monitoring method prevents a meaningful analysis of the patient's progress. In contrast, the present invention allows the second group outputs to be normalized with the first group outputs for a direct comparison. Again, the instrumentation differences between the laboratory group results are mitigated, which is beneficial for a mobile patient.

In yet another embodiment, the method and device of the present invention allows an individual laboratory group to map a chain of laboratory instruments outputs according to a standardized output value as the outputs are generated. In this embodiment, a LIS (FIG. 1) within the group of laboratory instruments receives a desired value range in which to report the outputs from its laboratory instruments. As the LIS receives outputs from the various laboratory instruments in the group, it normalizes the outputs according to the desired value range prior to outputting the output from the group. Thus, the normalizing functionality is built into the LIS for real time processing. As would be readily understood, the normalized output from the LIS could then be further implemented in other normalization functions such as those described in the first and second embodiments.

In general, the normalization system of the present invention allows groups of laboratory instruments to submit outputs indicative of the laboratory instrument testing results to the normalization server and have the outputs normalized according to a control group. The normalized outputs can then be utilized to compare the current results with a previous test and/or to calibrate the group of laboratory instruments according to a peer group. Additionally, while many program languages could be used to create the objects and functions of the present invention, the present invention is preferably coded by an object-oriented language such as Microsoft Corporation's "VISUAL C++®" OR "VISUAL BASIC®" programming languages.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative, and not in a limiting sense.

I claim:

1. A system for normalizing groups of laboratory instruments, the system comprising:
    one or more groups of laboratory instruments; and
    a normalization server in communication with the groups of laboratory instrument,
    wherein the groups of laboratory instruments comprise a laboratory information system coupled to individual laboratory instruments and in communication with the normalization server and wherein the groups of laboratory instruments send data indicative of outputs to the normalization system, and wherein the normalization system outputs normalized outputs to the groups of laboratory intruments.

* * * * *